US00PP31409P2

(12) United States Plant Patent
Ranney

(10) Patent No.: US PP31,409 P2
(45) Date of Patent: Jan. 28, 2020

(54) ***PYRACOMELES VILMORINII* PLANT NAMED 'NCXP1'**

(50) Latin Name: *Pyracomeles vilmorinii*
Varietal Denomination: NCXP1

(71) Applicant: North Carolina State University, Raleigh, NC (US)

(72) Inventor: Thomas Green Ranney, Arden, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 15/999,227

(22) Filed: Aug. 16, 2018

(51) Int. Cl.
*A01H 6/74* (2018.01)
*A01H 5/00* (2018.01)

(52) U.S. Cl.
USPC ..... Plt./226

(58) Field of Classification Search
USPC ..... Plt./226
CPC ..... A01H 6/74; A01H 5/00
See application file for complete search history.

*Primary Examiner* — Keith O. Robinson
(74) *Attorney, Agent, or Firm* — Cassandra Bright

(57) ABSTRACT

A new and distinct *Pyracomeles* cultivar named 'NCXP1' is disclosed, characterized by thornless shoots and a compact, dense, spreading plant habit. Plants are non-flowering after 8 years of observation. The new cultivar is a *Pyracomeles*, suitable for ornamental garden purposes.

2 Drawing Sheets

Latin name of the genus and species: *Pyracomeles vilmorinii.*

Variety denomination: 'NCXP1'.

BACKGROUND OF THE INVENTION

The present invention comprises a new and distinct *Pyracomeles vilmorinii* cultivar hereinafter referred to by the cultivar name 'NCXP1'. This new *Pyracomeles vilmorinii* was developed through a breeding program at a research nursery, located in Mills River, N.C. In 2001, the seed parent, *Pyracomeles vilmorinii* (*Pyracantha crenatoserrata* x *Osteomeles subrotunda*), unpatented, unnamed was hybridized with the pollen parent *Pyracantha crenatoserrata* (*fortuneana*) 'Cherri Berri' to create a population (H2002-019) of new hybrids. Seeds from open pollinated plants of H2002-019 were germinated in 2010 to create a new population, H2010-272. 'NCXP1' was selected from the H2010-272 population, based upon its combination of desirable traits as described below.

The first asexual propagation of 'NCXP1' occurred in July 2010 by rooting stem cuttings at the North Carolina State University Mountain Horticultural Crops Research Station, Mills River, N.C. 'NCXP1' roots readily from softwood cuttings treated with a basal dip of 5,000 ppm indole butyric acid (potassium salt) in water. 'NCXP1' was has been repeatedly reproduced by vegetative cuttings over an 8 year period and has been found to retain its distinctive characteristics through successive asexual propagations.

SUMMARY OF THE INVENTION

The following are the unique combination of characteristics of this new cultivar when grown under standard horticultural practices at Mills River, N.C.

1. Compact, spreading habit.
2. Thornlessness.
3. Showy, evergreen foliage.

COMPARISON TO PARENT VARIETIES

*Pyracomeles vilmorinii* 'NCXP1' is a unique intergeneric hybrid, which confers significant differences in habit, form, and plant morphology when compared to its parental taxa. 'NCXP1' is distinct from the pollen parent in that 'NCXP1' is thornless and has a much more compact, spreading habit.

This new hybrid is distinct from the seed parent in that 'NCXP1' has mostly entire (sometimes crenulate or serrate; rarely with occasional clefts) leaves while the seed parent is most likely to have pinnate leaves.

Additionally, 'NCXP1' is free of flowers and fruit, unlike either parental taxa.

COMMERCIAL COMPARISON

'NCXP1' can be compared to the unpatented, unnamed *Pyracomeles vilmorinii* known in the industry and academia. Plants of the new cultivar 'NCXP1', differ in the following:

1. Plants of the new variety have not been observed to produce flowers, this comparator produces flowers.
2. Foliage of the new variety is long and more linear than the smaller, more elliptic to nearly round leaves found on this comparator.
3. Foliage of the new variety is simple, foliage of this comparator is compound.

'NCXP1' can be compared to the unpatented *Pyracomeles coccinea* 'Lowboy'. Plants of the new cultivar 'NCXP1', differ in the following:

1. Plants of the new variety have not been observed to produce flowers, this comparator produces flowers.
2. Foliage of the new variety is glossier than leaves found on this comparator.
3. Plants of the new variety are shorter and more compact than plants of this comparator.

BRIEF DESCRIPTION OF THE PHOTOGRAPHS

Flowers, foliage, and form of 'NCXP1' illustrated by the accompanying photographs which show the plant's form and foliage. The colors shown are as true as can be reasonably obtained by conventional photographic procedures. Colors in the photographs may differ slightly from the color values cited in the detailed botanical description, which accurately describe the colors of the new *Pyracomeles vilmorinii* 'NCXP1'.

DETAILED BOTANICAL DESCRIPTION

Figure 1:
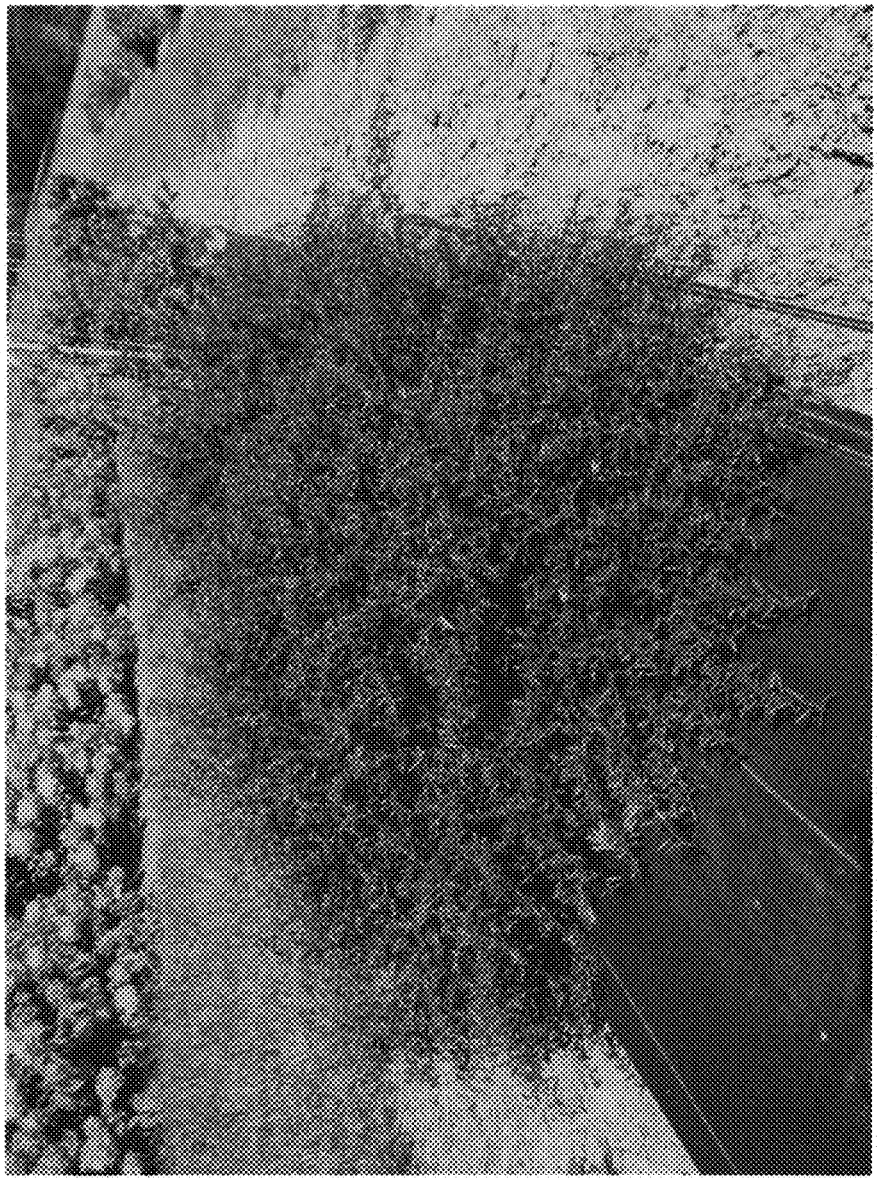
FIG. 1 is a photograph showing the form and habit of a 5-year-old 'NCXP1' in Mills River, N.C., in October, 2016.
Figure 2:
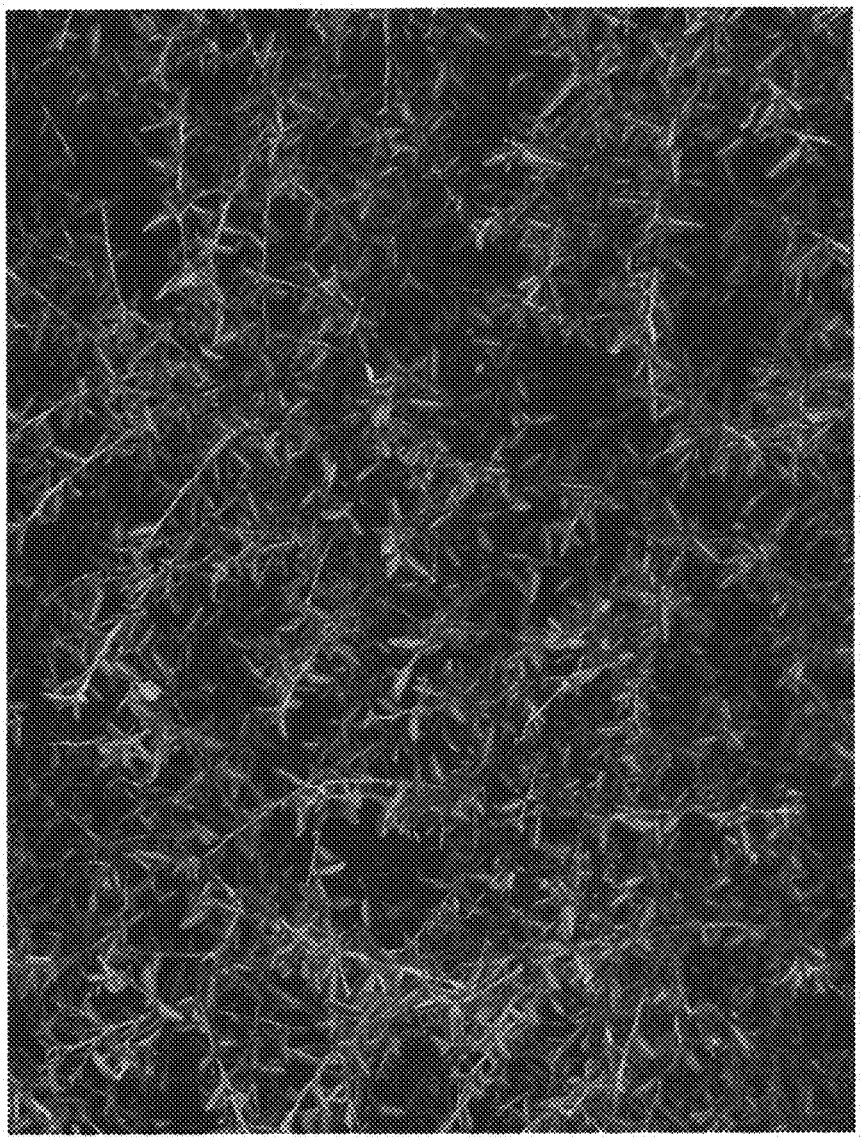
FIG. 2 is a photograph showing the foliage and winter foliage colors of a 6-year-old 'NCPX1' in Mills River, N.C., in December, 2017.

The following is a detailed description of the botanical characteristics of the new and distinct *Pyracomeles vilmorinii* 'NCXP1'. The description was taken in 2017 on a 5-year-old, field-grown plant in Mills River, N.C. All colors cited herein refer to The Royal Horticultural Society Colour Chart (The Royal Horticultural Society (R.H.S.), London, 2015 Edition. Where specific dimensions, sizes, colors, and other characteristics are given, it is to be understood that such characteristics are approximations or averages set forth as accurately as practicable.

Botanical classification: *Pyracomeles vilmorinii* 'NCXP1'.

PROPAGATION

Typically by softwood stem cuttings.

PLANT

Plant type and growth habit: Compact and spreading; densely multi-stemmed evergreen shrub.

Height: About 0.5 m at 5 years.

Width: About 1 m at 5 years.

Growth rate: Moderate.

Roots: Fibrous.

Shoots (most recent year's growth):

*Shape*.—Rounded.

*Thorns*.—Thornless.

*Immature shoots*.—In the sun, new growth at the union point ranges from RHS 166A-176A (Greyed Orange Group), transitioning to RHS 183A-183C (Greyed Purple Group) with new growth tips exhibiting coloration within the RHS 187A-187C (Greyed Purple Group) range. In the shade, new growth shoots are more consistent in color, generally falling within the RHS N199A (Dark Greyish Yellowish Brown) designation.

*Mature shoot*.—Shoot color is variable and dependent on exposure to sunlight and stage of maturity. Mature shoots exposed to sunlight exhibit RHS 199B (Light Olive Brown) coloration at branch union points, which transitions to RHS N199C (Moderate Yellowish Brown) at the tips. In the shade, mature shoots are generally RHS 199A (Dark Greyish Yellowish Brown) at branch union points, and fade to RHS N199C (Moderate Yellowish Brown) at shoot tips.

*Shoot texture*.—Slightly pubescent with fine, silver (too minute to measure accurately with R.H.S. chart) hairs visible under magnification; raised lenticels are visible and are more apparent on stems exposed to direct sunlight.

*Lenticels*.—Color: RHS 165C (Moderate Orange Yellow). Diameter: Average is 0.5 mm (range is 0.3-0.8 mm).

*Internode length*.—Average is 16.9 mm (range is 15-20 mm).

*Shoot length*.—Average is 10.0 cm (range is 7.2-12.9 cm).

*Shoot diameter*.—Average is 0.96 mm (range is 0.52-1.37 mm).

Branches:

*Diameter*.—Fully mature branches range from 2-4 cm in diameter.

*Color*.—Mix of RHS N200B (Brownish Grey) and RHS N200C (Light Brownish Grey).

FOLIAGE

Leaf:

*Type*.—Simple.

*Arrangement*.—Alternate; with age, sometimes whorled.

*Persistence*.—Evergreen.

*Shape*.—Leaves exposed to direct sunlight were variable in shape. Generally, leaves are elliptic and oblong with occasional oblanceolate and obovate leaf shapes. In the shade, leaves were often elliptic, obovate or oblong with occasional oblanceolate leaves.

*Apex*.—Variable: ranges from rounded to broadly acute, occasionally apices are obtuse or cuspidate; rarely, some apices are emarginate.

*Base*.—Generally cuneate or rounded.

*Margin*.—Variable: ranges from entire to crenulate or serrate; in the shade, serration deepens to form occasional clefts.

*Venation*.—Reticulate.

*Texture*.—Glabrous, glossy adaxial surface; glabrous abaxial surface.

*Size*.—Length: Average is 15.9 mm (range 10-25 mm). Width: Average is 6.60 mm (range is 4-12 mm).

*Attachment*.—Petiolate.

*Immature leaf color*.—As with mature leaves, immature leaves exhibit color variation in response to sunlight. In the sun, adaxial surfaces exhibit RHS 141A (Deep Yellowish Green) at the leaf base, and transition to RHS 139A (Dark Yellowish Green). Leaf tips range from RHS 183B to RHS 187A (Dark Red). Abaxial surfaces are RHS 165A (Moderate Brown). In the shade, adaxial surfaces range from RHS 143A to RHS 144A (Strong Yellow Green) at the leaf base, and exhibit blushing along the leaf margins and tips in RHS N34B (Strong Reddish Orange). Abaxial surfaces are RHS N144A (Strong Yellowish Green). In winter, the youngest leaves often turn RHS 179A (Moderate Red).

*Mature leaf color*.—Color: Leaf color is variable depending upon sun exposure. In the sun, adaxial surfaces are generally a mix of RHS 143B (Deep Yellowish Green) and RHS 39A (Dark Yellowish Green). Adaxial surfaces exhibit RHS 146D (Moderate Yellow Green) coloration. In the shade, adaxial surfaces are a mix of RHS 139B (Moderate Yellowish Green) and RHS 141B (Deep Yellowish Green) while abaxial surfaces are a mix of RHS 146C and RHS 146D (Moderate Yellow Green).

*Petiole*.—Shape: Rounded. Length: Average is 1.45 mm (range is 0.7-2.50 mm). Diameter: Average is 0.52 mm (range is 0.30-1.00 mm). Surface: Glabrous. Color: Green 139A (Dark Yellowish Green).

*Stipules*.—Are minute and exist as pairs, and require magnification for visibility. They are approximately 0.1×0.2 mm.

FLOWER

'NCXP1' has not exhibited flowers or fruit in 8 years of observation.

OTHER CHARACTERISTICS

Disease and pest resistance: Not observed to be susceptible nor resistant to normal diseases and pests of *Pyracomeles*.

Temperature tolerance: Cold-hardy to USDA Zone 6A. Survival over multiple winters has also been documented in USDA Zone 5.

Fruit/seed production: Not observed to date.

What is claimed is:

1. A new and distinct cultivar of *Pyracomeles* plant named 'NCXP1' as herein illustrated and described.

* * * * *